(12) United States Patent
Coussios et al.

(10) Patent No.: US 9,662,089 B2
(45) Date of Patent: *May 30, 2017

(54) MAPPING AND CHARACTERIZATION OF CAVITATION ACTIVITY

(71) Applicant: Isis Innovation Limited, Summertown, Oxford (GB)

(72) Inventors: Constantin C. Coussios, Oxford (GB); Miklos Gyongy, Oxford (GB); Manish Arora, Oxford (GB); Ronald Aurele Roy, Boston, MA (US)

(73) Assignee: Oxford University Innovation Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/964,895

(22) Filed: Dec. 10, 2015

(65) Prior Publication Data

US 2016/0089109 A1 Mar. 31, 2016

Related U.S. Application Data

(63) Continuation of application No. 12/998,571, filed as application No. PCT/GB2009/051482 on Nov. 4, 2009, now Pat. No. 9,238,152.

(Continued)

(30) Foreign Application Priority Data

Nov. 7, 2008 (GB) .................................. 0820377.0
Nov. 4, 2009 (WO) ................ PCT/GB2009/051482

(51) Int. Cl.
*A61B 8/08* (2006.01)
*A61N 7/02* (2006.01)
(Continued)

(52) U.S. Cl.
CPC .................. *A61B 8/08* (2013.01); *A61N 7/00* (2013.01); *A61N 7/02* (2013.01);
(Continued)

(58) Field of Classification Search
CPC ..................................... A61B 8/00; A61B 8/08
See application file for complete search history.

(56) References Cited

U.S. PATENT DOCUMENTS 4,075,883 A * 2/1978 Glover ................. A61B 8/0825
378/17
5,158,071 A 10/1992 Umemura et al.
(Continued)

FOREIGN PATENT DOCUMENTS

CN 101119767 A 2/2006
CN 1864636 A 11/2006
(Continued)

OTHER PUBLICATIONS

Office Action for corresponding Japanese Patent Application No. 2015-026320 dated Jan. 28, 2016.
(Continued)

*Primary Examiner* — Peter Luong
(74) *Attorney, Agent, or Firm* — Wegman, Hessler & Vanderburg

(57) ABSTRACT

Apparatus for locating bubbles in a subject comprises a plurality of pressure wave detectors arranged to operate as passive detectors to generate output signals in response to the receipt of pressure waves generated at a source comprising at least one bubble, and processing means arranged to receive signals from the detectors and to determine from the signals the position of the source.

31 Claims, 9 Drawing Sheets

Related U.S. Application Data

(60) Provisional application No. 61/111,646, filed on Nov. 5, 2008.

(51) Int. Cl.
*A61N 7/00* (2006.01)
*A61B 17/00* (2006.01)
*A61B 17/22* (2006.01)
*A61B 90/00* (2016.01)

(52) U.S. Cl.
CPC ............... *A61B 2017/00106* (2013.01); *A61B 2017/22008* (2013.01); *A61B 2090/378* (2016.02); *A61N 2007/0052* (2013.01)

(56) References Cited

U.S. PATENT DOCUMENTS

| | | | |
|---|---|---|---|
| 5,733,527 | A | 3/1998 | Schutt |
| 6,508,774 | B1 | 1/2003 | Acker et al. |
| 2003/0130599 | A1 | 7/2003 | Restle et al. |
| 2004/0039312 | A1 | 2/2004 | Hillstead et al. |
| 2006/0184075 | A1 | 8/2006 | Restle et al. |
| 2007/0038099 | A1 | 2/2007 | Sugita et al. |
| 2007/0083120 | A1 | 4/2007 | Cain et al. |
| 2007/0161902 | A1 | 7/2007 | Dan |
| 2008/0015435 | A1 | 1/2008 | Cribbs et al. |

FOREIGN PATENT DOCUMENTS

| | | |
|---|---|---|
| CN | 1864836 A | 11/2006 |
| CN | 1891167 A | 1/2007 |
| EP | 1712182 A1 | 10/2006 |
| EP | 1 723 911 A1 | 11/2006 |
| JP | H2-126848 | 5/1990 |
| JP | 2002-224127 | 8/2002 |
| JP | 2005-517488 | 6/2005 |
| JP | 2007-520327 A | 7/2007 |
| WO | WO 91/15999 | 10/1991 |
| WO | 03/070105 | 8/2003 |
| WO | WO 2008143998 A1 | 11/2008 |

OTHER PUBLICATIONS

International Search Report and Written Opinion mailed Mar. 26, 2010 for PCT/GB2009/051482 filed Nov. 4, 2009.
International Preliminary Report on Patentability mailed May 10, 2011 for PCT/GB2009/051482 filed Nov. 4, 2009.
Search Report Under Section 17(6) mailed Oct. 23, 2009 for GB0820377.0 filed Nov. 7, 2008.
Coussios, C.C. et al., "Role of Acoustic Cavitation in the Delivery and Monitoring of Cancer Treatment by High-Intensity Focused Ultrasound (HIFU)", International Journal of Hyperthermia, vol. 23, pp. 105-120, 2007.
Farny, C.H. et al., "Monitoring the Development of HIFU-Induced Cavitation Activity", AIP Conf. Proc., vol. 829, pp. 348-352, 2006.
Vaezy, S. et al., "Real-Time Visualization of High-Intensity Focused Ultrasound Treatment Using Ultrasound Imaging", Ultrasound Med. Biol., vol. 27, pp. 33-42, 2001.
Rabkin, B.A. et al., "Hyperecho in Ultrasound Images of HIFU Therapy: Involvement of Cavitation", Ultrasound Med. Biol., vol. 31, pp. 947-956, 2005.
Norton, S.J. et al., "Passive Imaging of Underground Acoustic Sources", J. Acoust. Soc. Am., vol. 119, pp. 2840-2847, 2006.
Rabkin, B.A. et al., "Biological and Physical Mechanisms of HIFU-Induced Hyperecho in Ultrasound Images", Ultrasound in Medicine & Biology, 32(11), pp. 1721-1729, 2006.
Lafon, C. et al., "Gel Phantom for Use in High-Intensity Focused Ultrasound Dosimetry", Ultrasound in Medicine and Biology, 31(10), pp. 1383-1389, 2005.
Second Office Action mailed Mar. 26, 2014 in Chinese Patent Application No. 200980153786.8.
Japanese Office Action mailed Nov. 14, 2013 for Japanese Patent Application No. JP 2011-533834.
Decision of Rejection, JP2011-533834; Date Mailed: Oct. 14, 2014; Patent Office Examiner: Tomoya Sato 3735 3I00; Title of Invention: Mapping and Characterization of Cavitation Activity; Reference No. Dispatch No. 541243; pp. 1-2.
Chinese Patent Application No. 2009801537868; Text of the Third Office Action PUD71960A; Examination Department: Electronics Invention Examination Department, Beijing Patent Examination Cooperation Center; Sep. 17, 2014; pp. 1-22.
Quingge Pan, etc. Radar Science and Techniques, Dec. 31, 2005; pp. 332-335, vol. 3, period 6.

\* cited by examiner

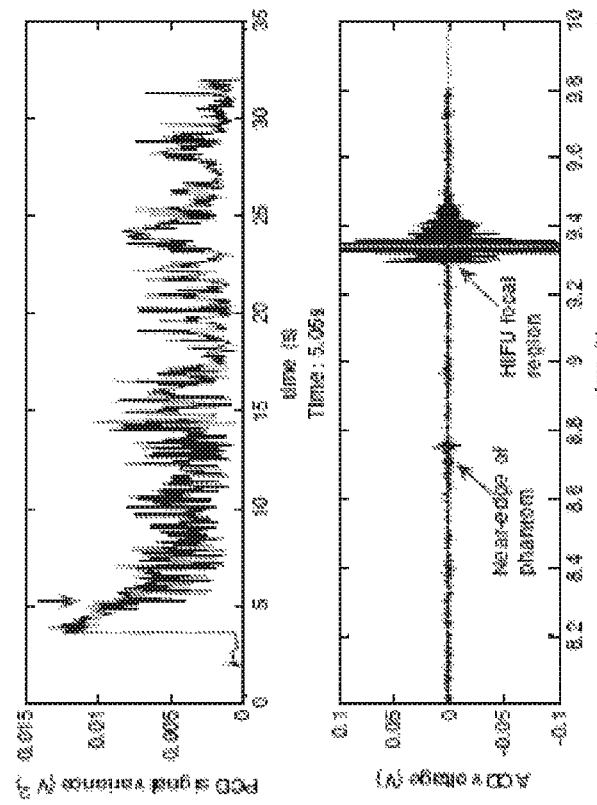
Fig. 11a
Fig. 11b
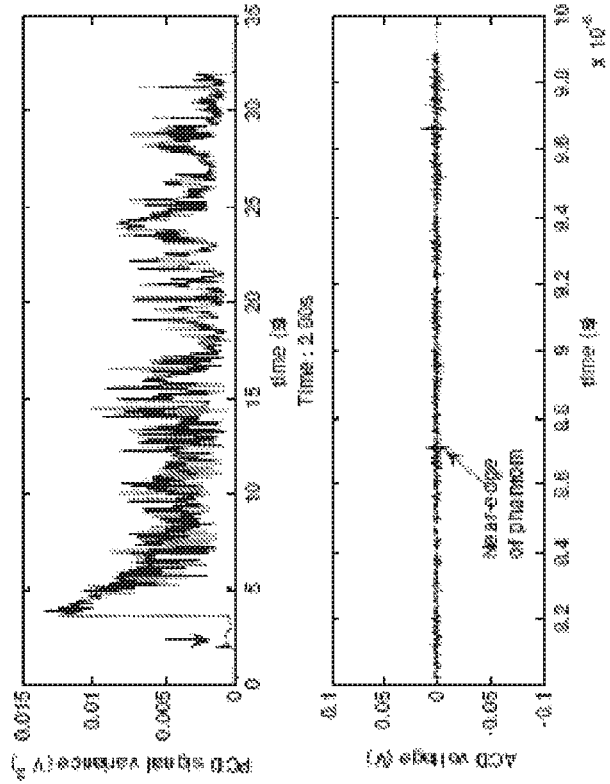
Fig. 11c
Fig. 11d

MAPPING AND CHARACTERIZATION OF CAVITATION ACTIVITY

CROSS-REFERENCE TO RELATED APPLICATIONS

This application claims the priority filing benefit of U.S. patent application Ser. No. 12/998,571 filed Oct. 19, 2011; International PCT Application PCT/GB2009/051482 filed Nov. 4, 2009 and published under PCT 21(2) in the English language; U.S. Provisional Patent Application Ser. No. 61/111,646 filed Nov. 5, 2008; and Great Britain Patent Application Serial No. 0820377.0 filed Nov. 7, 2008, all of which are incorporated by reference herein.

FIELD OF INVENTION

The present invention relates to the localization, mapping and characterization of bubbles which act as acoustic sources radiating pressure/density perturbations at any frequency or set of frequencies. It has particular application in the monitoring of therapeutic ultrasound treatment but can also be used, for example, in diagnostic ultrasound systems and photoacoustic imaging.

BACKGROUND OF THE INVENTION

The use of high intensity focused ultrasound (HIFU) for cancer therapy has several major advantages over other, more established treatment modalities: it is cheap, non-invasive, and has minimal side-effects. However, widespread acceptance of HIFU is hindered by the lack of a reliable real-time monitoring system.

Above a certain pressure threshold, high-amplitude acoustic waves propagating through tissue can spontaneously nucleate and excite small, micron-sized bubbles, a phenomenon known as acoustic cavitation. The cavitating bubbles re-emit part of the incident ultrasound over a range of frequencies that are different to the HIFU excitation frequency, which is useful for two reasons. Firstly, emissions that have a higher frequency content than the original HIFU source will be absorbed more readily by surrounding tissue, which means that cavitation can greatly enhance heat deposition [Coussios C C, Farny C H, Haar G T, Roy R A. "Role of acoustic cavitation in the delivery and monitoring of cancer treatment by high-intensity focused ultrasound (HIFU)", International Journal of Hyperthermia vol. 23, pp 105-120, 2007]. Secondly, the broadband acoustic emissions that are associated with this enhanced heating can serve as an indicator of treatment.

Cavitation during HIFU exposure has previously been monitored in either of two ways. One option is to use high-frequency broadband transducers to act as passive cavitation detectors (PCDs) that record the acoustic emissions from cavitating bubbles [C. H. Farny, R. G. Holt, R. A. Roy, "Monitoring the development of HIFU-induced cavitation activity," AIP Conf. Proc., vol. 829, pp. 348-352, 2006]. PCDs have a fixed focus, however, thereby providing information for a fixed region only. It should be noted that there is currently no cavitation monitoring system that has been adopted in clinical practice. Alternatively, hyperechogenic regions in B-mode ultrasound images can enable detection and localization of bubble activity using time-of-flight information [S. Vaezy, et al., "Real-time visualization of high-intensity focused ultrasound treatment using ultrasound imaging", Ultrasound Med. Biol., vol. 27, pp. 33-42, 2001]. However, B-mode images can only be taken while the HIFU is off to avoid interference from the therapeutic ultrasound signal and will thus only enable detection of cavities that subsist after HIFU excitation has ceased. B-mode monitoring is therefore less sensitive than PCD monitoring, and has been previously shown to be detecting boiling bubbles that are indicative of overtreatment, rather than inertially cavitating bubbles that are indicative of enhanced heat deposition [B. A. Rabkin, V. Zderic, S. Vaezy, "Hyperecho in ultrasound images of HIFU therapy: involvement of cavitation," Ultrasound Med. Biol., vol. 31, pp. 947-956, 2005].

SUMMARY OF THE INVENTION

The present invention provides apparatus for locating bubbles in a subject. The apparatus may comprise a plurality of pressure wave detectors, which may be sound detectors, arranged to operate as passive detectors. The detectors may be arranged to generate output signals in response to the receipt of pressure waves, which may be in the form of sound, generated at a source. The source may comprise at least one bubble. The apparatus may further comprise processing means arranged to receive signals from the detectors and to determine from the signals the position of the source.

The invention can be used across a broad range of therapeutic, diagnostic and other ultrasound applications, including drug delivery systems. Some of these are High Intensity Focused Ultrasound (HIFU). In other applications, for example, in the context of drug delivery, pressure waves with amplitudes that are in-between those used for diagnostic ultrasound and HIFU are used. Indeed the invention can be used with pressure waves at sound frequencies outside the ultrasound range, including audible sound and infrasound. For example boiling bubbles generated during therapeutic ultrasound treatment can generate audible sound, which can be detected and used to locate and map the cavitation.

The apparatus may further comprise an ultrasound generator arranged to generate ultrasound at a generator frequency. The detectors may be arranged to detect ultrasound at least one detection frequency which is different from the generator frequency. The at least one detection frequency may comprise a range of detection frequencies, the generator frequency being outside the range. The range of frequencies that the detectors can detect may, for example, be determined by one or more filters arranged to filter the detector signal. Alternatively, or in addition, it may be determined by the nature of the detectors themselves.

The detectors may be arranged to detect ultrasound while the generator is active. The processing means may be arranged to determine a position of the source, which is a position of the source at a time when the generator is active.

The generator may be a therapeutic ultrasound generator. The apparatus may comprise a diagnostic ultrasound generator arranged to generate ultrasound at a diagnostic frequency different from the generator frequency. The apparatus may comprise an active ultrasound detector arranged to detect ultrasound at the diagnostic frequency. The diagnostic generator may be a transducer which also acts as the active ultrasound detector, or it may be a separate generator. The processing means may be arranged to receive signals from the active ultrasound detector.

At least one of the passive ultrasound detectors may be arranged to operate alternatively as the active ultrasound detector. The passive ultrasound detectors may comprise an array of detectors each of which can be operated alternatively as an active ultrasound detector. This allows the apparatus to switch between different modes, for example an active mode and a passive mode, and to use data from both of the modes to locate or characterize the cavitation. This is possible because what determines whether a detector is acting as an active or a passive detector is at least partly the type of processing that is performed on the signals from the sensor, as is described in more detail below. Therefore the processing means can be arranged to perform two or more different processing algorithms or methods on the detector signals, which allows the processing means, and therefore the detectors, to be operated in active or passive modes as required.

The source may comprise a single bubble. The processing means may be arranged to determine the position of the bubble. The processing means may be arranged to determine the position of the bubble from the arrival times of ultrasound signals at the detectors.

The source may comprise a plurality of bubbles and the processing means may be arranged to process the signals to generate a map of the source. For example the map may be generated by determining an intensity at each of a plurality of positions from the detector signals using a relationship of the form:

$$I = \frac{1}{T}\int_0^T \left[\left(\sum_i H_i(\tau)\right)^2 - \sum_i H_i(\tau)^2\right] d\tau$$

where $\tau$ represents a dummy integration variable used to integrate the plurality of signals $H_i(t)$, which represent the backpropagated signals received from the source(s) by each ultrasound detector, and T represents an arbitrary integration time interval.

The processing means may be arranged to turn on the ultrasound generator and to measure the time at which the detectors detect ultrasound. The processing means may thereby to determine the location of the source.

Indeed the present invention further provides apparatus for locating an ultrasound source comprising at least one bubble, the apparatus comprising an ultrasound transducer and a passive ultrasound detector, and control means arranged to turn the ultrasound transducer on and measure the time at which the passive detector detects ultrasound thereby to determine the location of the source. The transducer may be a therapeutic transducer and may be turned on and off repeatedly during treatment of a patient, for example in a duty cycle of 90% or 95%.

The processing means may be arranged to analyze at least two different frequency components of the signals to determine a characteristic of the source. One of the frequency components may be a broadband component. One of the frequency components may include at least one harmonic or sub-harmonic of a generator frequency, and preferably a plurality of harmonic or sub-harmonic frequencies. The broadband component may be obtained by filtering out components of the detector signals which are at the generator frequency and harmonics of the generator frequency, and optionally sub-harmonics of the generator frequency also.

The processing means may be arranged to filter out components of the detector signals at harmonics of the frequency of the generator thereby to produce a filtered signal, and to determine the position of the source from the filtered signal.

The present invention further provides a method of locating bubbles in a subject, the method comprising receiving ultrasound signals, generated at a source comprising at least one bubble, at each of a plurality of passive ultrasound detectors, generating output signals from each of the detectors in response to the receipt of the ultrasound, and processing the signals to determine the position of the source.

Where ultrasound is referred to pressure waves, which may be in the form of sound of other frequencies can also be used where appropriate.

In order to exploit the advantages of both previous approaches, some embodiments of the present invention provide a system that can effectively act as an array of PCDs that can be electronically focused in order to provide spatial resolution. In some embodiments the system is capable of localizing single bubble activity, and in some embodiments the system can provide mapping of an extended cavitating region or of several, disjoint cavitating regions.

Preferred embodiments of the present invention will now be described by way of example only with reference to the accompanying drawings.

BRIEF DESCRIPTION OF THE DRAWINGS

FIGS. 11a to 11d are a set of graphs showing passive and active cavitation detection in the system of FIG. 2 using signals received by one of the elements.

DESCRIPTION OF THE PREFERRED EMBODIMENTS

Figure 1:
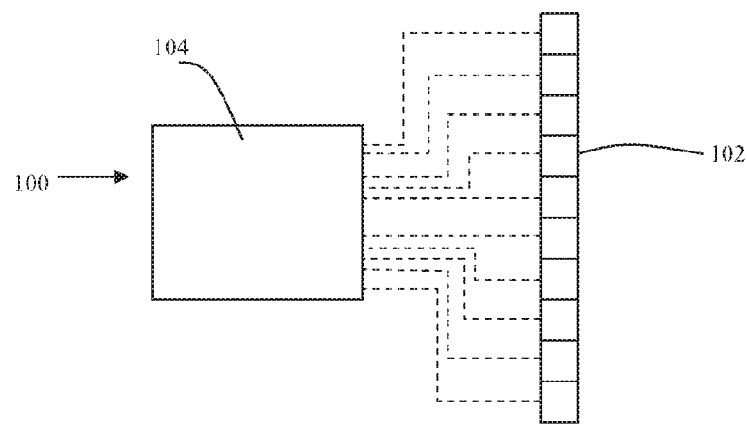
FIG. 1 is a schematic diagram of an ultrasound system according to an embodiment of the invention.

Referring to FIG. 1, a diagnostic ultrasound system 100 according to a first embodiment of the invention comprises an array of vibration detectors, which in this case are pressure wave detectors arranged to detect sound, specifically ultrasound detectors 102 each of which is arranged to generate an output signal dependent on the amplitude and frequency of pressure waves it detects, in this case within a range of ultrasound frequencies. The detectors are non-focused, each being arranged to detect ultrasound signals from a wide range of angles. Each of the detector output signals is received by a processing system 104 which is arranged to process the received signals and to determine from them the location of the source of the ultrasound. In this embodiment the range of ultrasound frequencies which can be detected is 5-10 MHz, but it will be appreciated that this range can vary depending on the system. The system in this embodiment is arranged to be used in conjunction with a therapeutic ultrasound system which operates at a frequency range of 500 kHz. This means that the system 100 can be used to monitor cavitation caused by the therapeutic ultrasound while the therapeutic ultrasound is being generated. The analysis of the signals received by this system can be the same as the embodiment of FIG. 2, and will be described in more detail with reference to that Figure.

Figure 2:
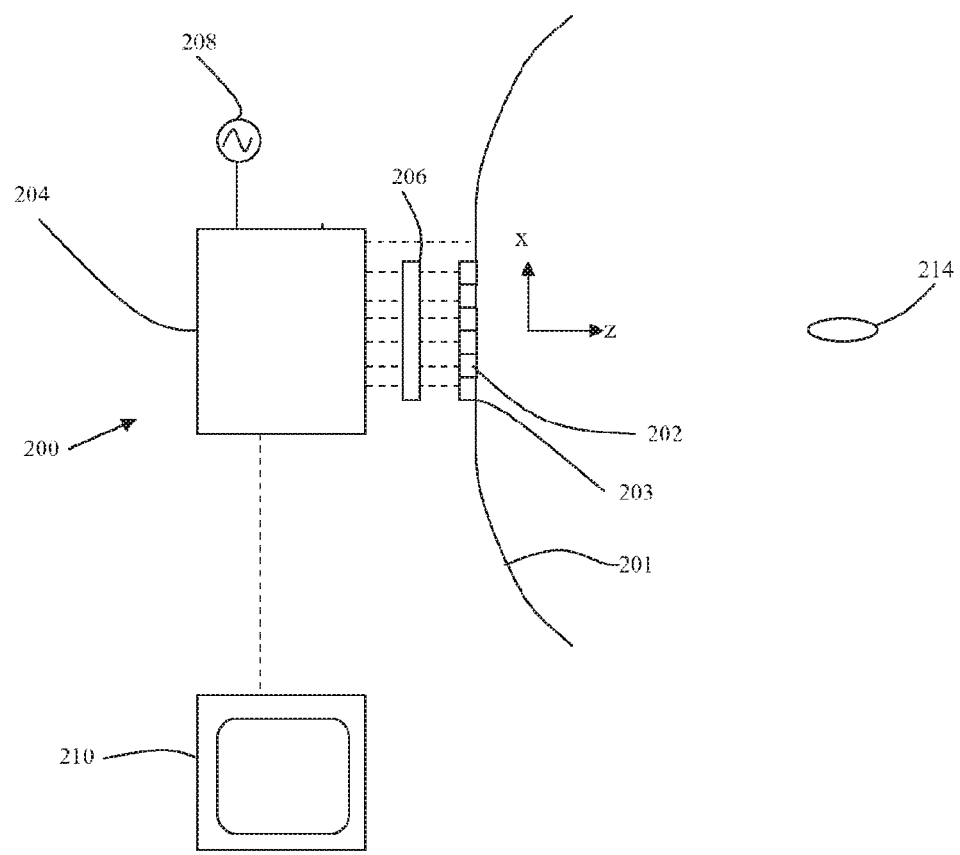
FIG. 2 is a schematic diagram of an ultrasound system according to a further embodiment of the invention.

Referring to FIG. 2, in a second embodiment of the invention an ultrasound system 200 comprises a therapeutic ultrasound transducer 201, with an array of ultrasound detectors 202 positioned in an aperture 203 in the centre of the transducer 201. Each of the detectors 202 comprises a transducer which can be operated to generate ultrasonic signals and also to detect ultrasonic signals. They can therefore be used in an active mode in which they generate and detect ultrasound signals, or in a passive mode in which they only detect ultrasound signals. The array is a linear array extending in a direction which will be referred to as the x direction as shown in FIG. 2. The direction, perpendicular to the x direction, along the axis of the transducer will be referred to as the z direction. The imaging plane of the array is therefore the x-z plane. The direction perpendicular to both the x and z directions will be referred to as the y direction.

A control unit 204 is arranged to control generation of ultrasound signals by each of the transducer elements 202 and to receive the detector signals from each of the transducer elements 202 via a pre-amplifier and filter block 206. The control unit 204 is also arranged to control the transducer 201 to control the power and frequency of the ultrasound generated by the transducer 201, using a signal from an oscillator 208 to control the frequency of the ultrasound. It will be appreciated that the control unit, while being described functionally, can be made up of a single processor, or two or more separate processors performing different functions, for example control and analyzing functions, within the system. The control unit is connected to a display screen 210 on which data derived from the detector signals can be displayed in a suitable format. In this case the therapeutic transducer 201 has a focus in a focal region 214, in which it will generate the highest intensity ultrasound.

While the arrangement of FIG. 2 can be implemented using a variety of components and systems that operate over a range of vibrational frequencies of sound, including ultrasound, infrasound and audible sound, in this embodiment a zone system (Zonare Medical Systems, CA), together with the 2008 Research Package, was used as this allows simultaneous 5 MHz band IQ data acquisition from 64 detector elements 202, which can be remodulated to RF. When the array was used in the passive mode, pulse transmission was switched off so that the array was acting on receive only. In some modes, one group of transducer elements 202 is used in the active mode and another group in the passive mode so that active and passive detection can be used simultaneously. To make the system clinically applicable, a modified HIFU transducer 201 (Sonic Concepts, Woodinville Wash.) was used that had a central aperture 203 for the linear detector array 202 (Zonare L10-5, 5-10 MHz, 38 mm aperture). An IQ band of 4.6-9.6 MHz was chosen for these experiments, the closest possible to the frequency band of the array. This setup is readily transferable to a HIFU operating unit as no extra space needs to be made for the array and the orientation between the HIFU transducer and array is fixed.

To evaluate the system's ability to localize and map cavitation, several HIFU operating regimes and tissue mimicking gels were used. Here two of these will be described. Firstly, a homogeneous 3% aqueous agar gel was prepared. The water was deionized and the mixture was degassed at −50 kPa for 30 minutes. Upon setting, the gel was exposed to 1.06 MHz HIFU (Sonic Concepts H-102B SN-22) at its cavitation threshold of 1.1 MPa peak negative pressure at the focus, so that a single cavitating source would be created.

Secondly, in order to get two known regions of cavitation, a similar gel was made but with two 1.6 mm channels running parallel and at a distance of 20 mm from each other. The channels were positioned so that they cut across the linear array's imaging plane, making two 1.6 mm diameter circles, and these circles were along the axis of the HIFU transducer 201 (500 kHz, Sonic Concepts H-107B SN-10), being 10 mm in front of, and 10 mm behind the HIFU focus. 0.5% talc solution was made to flow through both channels, which cavitates much more readily than agar. A 500 kHz transducer was chosen because the pressure does not drop significantly over a distance of 10 mm, so when driving the transducer at 0.6 MPa peak negative focal pressure, the cavitation threshold of agar is not exceeded (1.1 MPa at 500 kHz), while the threshold for talc solution (0.2 MPa at 500 kHz) is.

The theory behind the operation of the two embodiments of the invention will now be described. Active detection, which includes pulse-echo imaging, requires an ultrasound generator which is arranged to generate ultrasound, typically in a pulse, and an 'active' detector' which detects reflected or re-emitted ultrasound from a cavitation region, and a processing system which uses the time interval between the generation of the ultrasound and the detection of ultrasound in determining the position of detected cavitation. In contrast, in passive localization and mapping, there is no direct information about the propagation time from a source to a receiver. Instead, cross-correlation of signals from a pair of receivers can provide an estimate of the differential time of arrival (DTOA), i.e., the difference in arrival time at the receivers of a signal from a source. This enables the difference in distance between the receivers and the source to be estimated. By using a set of cross-correlation pairs, single source localization and extended source mapping is possible. It will be appreciated from this that a single detector can be operated in both active and passive detection, depending on the processing which is performed on the sensor signals. A further explanation of passive localization and imaging follows.

Single Bubble Localization

Take a linear array of detector elements focused in the y=0 plane and placed on the x-axis, with receivers at $x_1$, $x_2$, ... $x_N$. The region of interest for cavitation localization is in front of the array: y=0, $x_1 < x < x_N$, z>0. Suppose there is a single cavitating source at a position ($x_s, z_s$). The propagation distance from the source to an element at x, relative to the distance between the source and a reference element at $x_0$ is then $$[z_s^2+(x-x_s^2)]^{1/2}-[z_s^2+(x_0-x_s^2)]^{1/2}. \qquad (1)$$

Assuming linear propagation of sound with speed c, we use the Fresnel approximation to derive the time of arrival of the source to an element at x relative to the time of arrival to the reference element at $x_0$:

$$1/c \cdot (\alpha x^2 + \beta x + \gamma), \qquad (2)$$

where $\alpha = -1/(2z_s)$;

$\beta = x_s/z_s$; (3)

$\gamma = (x_0^2 - 2x_0 x_s)/(2z_s)$.

The above expressions lead to a simple and efficient algorithm for localizing a single source, which includes the following steps:
1. Calculate the differential times of arrival between elements at various positions x and a reference element $x_0$ using cross-correlations.
2. Fit a parabola (using least square error linear fitting) to the differential times of arrival, extracting the parabolic coefficients $\alpha$, $\alpha$, $\gamma$.
3. Use equation (3) to calculate source location $(x_s, z_s)$ from $\alpha$, $\alpha$.

Extended Cavitation Region Mapping

When there is an extended region of cavitation, spatial maps of cavitation are necessary. The approach taken in this embodiment of the invention is one of passive beamforming, namely Time Exposure Acoustics (TEA) used in passive seismic imaging [S. J. Norton, B. J. Carr, A. J. Witten, "Passive imaging of underground acoustic sources," J. Acoust. Soc. Am., vol. 119, pp. 2840-2847, 2006.] A summary of the algorithm follows. Assume we have a source field $s(x,z,t)$ with zero temporal mean, that causes the pressure field $p(x,z,t)$ to propagate according to the linear wave equation:

$$\nabla^2 p - \frac{1}{c^2} \frac{\partial^2 p}{\partial t^2} = -s(x, z, t),$$ (4)

To estimate the source intensity I (temporal mean of s squared) at a position $(x_s, z_s)$, the RF pressure signal $p_i(t)$ for each element i of the array is back-propagated, and the following combination of temporal and ensemble moments taken:

$$I = \frac{1}{T} \int_0^T \left[ \left( \sum_i H_i(\tau) \right)^2 - \sum_i H_i(\tau)^2 \right] d\tau,$$ (5)

where $H_i(\tau)$ is the back-propagated signal $H_i(\tau) = d_i \cdot p_i(t + d_i/c + \tau)$, (6)

where $\tau$ is a dummy integration variable and $\tau$ is an arbitrary integration time interval with d being the propagation distance from the point $(x_s, z_s)$ to array element i:

$d_i = [z_s^2 + (x - x_s^2)]^{1/2}$. (7)

Using the identity $$\left( \sum_i a_i \right)^2 - \sum_i a_i^2 = 2 \sum_{i<j} a_i a_j,$$ (8)

and changing the order of summation and integration, the intensity map I can be re-arranged to give $$I = \sum_{i<j} \left[ \frac{2}{T} \int_0^T H_i(\tau) H_j(\tau) d\tau \right].$$ (9)

Equation (9) shows that the intensity map also corresponds to summing over all pairs of cross-correlations of back-propagated signals $H_i(\tau)$—however, calculation of the intensity from (5) is computationally more efficient. It should also be noted that in addition to compensation of spherical spreading and propagation time, $H_i(\tau)$ can be filtered to deconvolve the receiver response, to whiten the signal in order to give sharper cross-correlations, or to apply a tomographic filter to compensate for frequency-dependent blurring. However, in the example described above filtering the signal caused no significant changes to the maps, as the signal was band-limited as described above.

Figure 3:
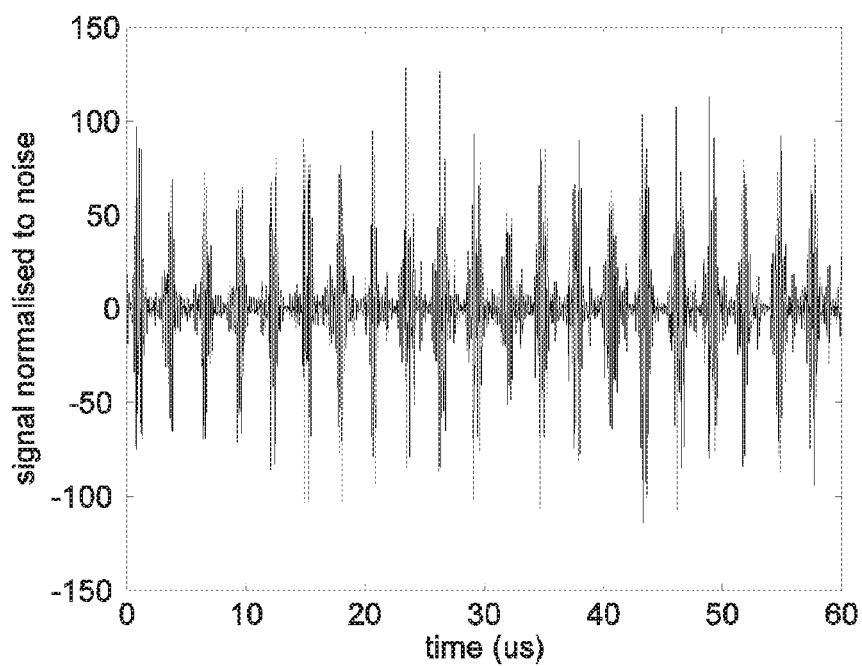
FIG. 3 is a graph showing a typical signal from one ultrasound detector forming part of the system of FIG. 2 received from a single-bubble source.
Figure 4:
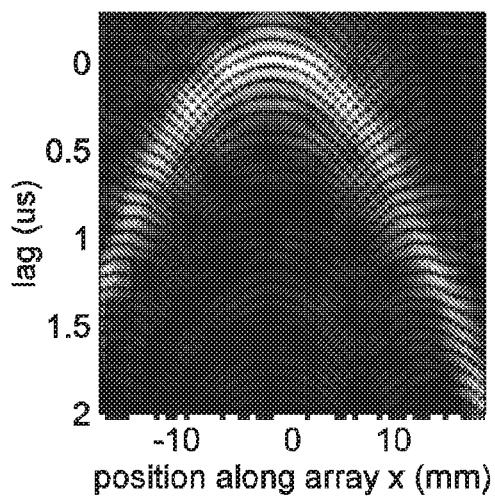
FIG. 4 is a graph showing arrival estimated time lag of an ultrasound signal as a function of position in the detector array of the system of FIG. 2.
Figure 5:
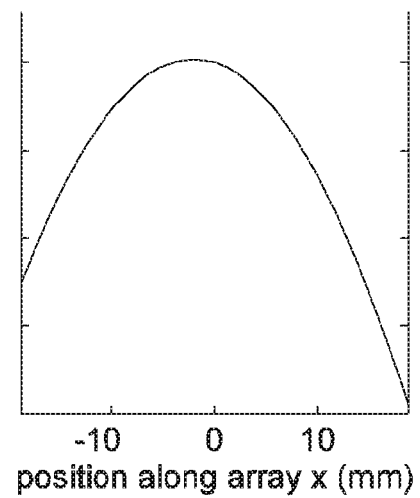
FIG. 5 is a curve fitted to the data of FIG. 4.

FIG. 3 shows a segment of an RF trace reconstructed from IQ data (4.6-9.6 MHz) from one of the detector elements 202 when the homogeneous agar phantom was insonified at its cavitation threshold. A periodic cavitation signal, corresponding to every third period of the 1.06 MHz cycle, can be clearly seen on each of the 64 detector elements, from which the presence of a single source can be inferred. Taking cross-correlations of the signal from a reference element with the signals from each of the 64 detector elements provides an indication of the delay in the signal from the source reaching each of the detector elements, and reveals a curved delay profile over the detector element array as shown in FIG. 4, to which a parabola can be fitted, as shown in FIG. 5. This profile can be used to determine the position of the source, using equation (3) as described above. In this example the source is located at 73.7 mm from the array, and −2.1 mm along the array. This is in agreement with where the 1.06 MHz HIFU focus was measured to be relative to the linear array using B-mode ultrasound.

Figure 6:
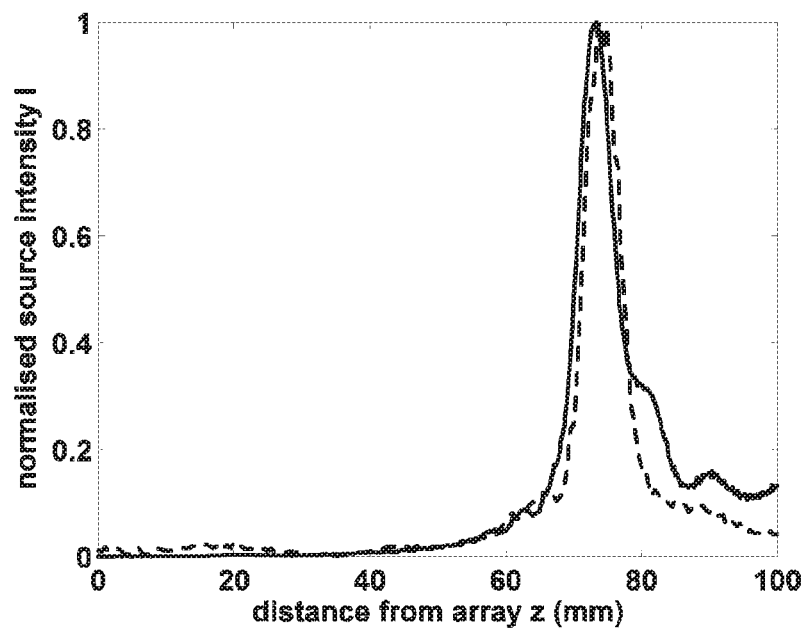
FIG. 6 is a mapping of intensity of ultrasound from a single bubble as a function of distance from the detector array of the system of FIG. 2.

In order to investigate the spatial resolution that can be achieved with a passive array, the algorithm for extended cavitation region mapping was applied to the case of a single-bubble source. Note that lateral resolution is significantly better than axial resolution, so FIG. 6 shows an axial cross-section of the intensity map, of single bubble data using time exposure acoustics (TEA), i.e., equation (9) above, together with a simulation of the map.

The simulation took a single bubble RF recording as the source, placed the source at the position estimated by the parabolic localization algorithm (−2.1,73.7) mm, and propagated the signal to the array elements. A source intensity map was then generated using TEA from this data. The solid line shows a map generated from actual single bubble recordings, while the dashed graph shows a simulated map. Note that because axial resolution is inversely proportional to axial distance squared (not proved here), much higher resolved maps could be generated by placing the array closer to the agar phantom. However, such a setup would no longer be clinically applicable.

Figure 7:
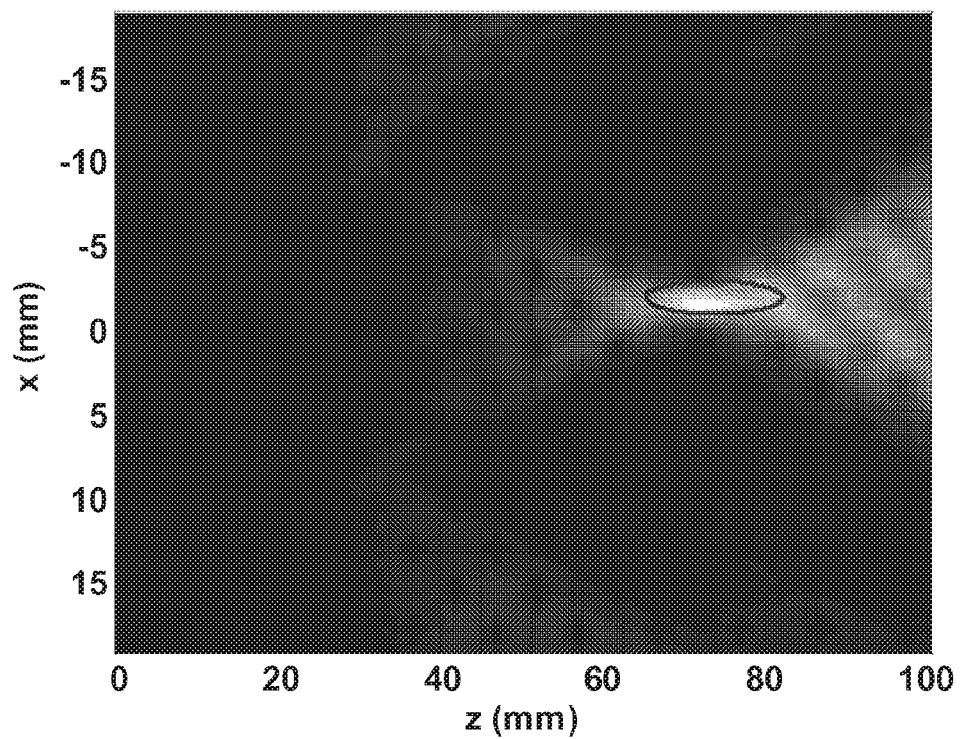
FIG. 7 is a two-dimensional mapping of cavitation produced by the system of FIG. 2.

The algorithm for extended cavitation region mapping was also applied to an extended cavitating region during HIFU exposure. The resulting intensity map is shown in FIG. 7, where it can be seen that the mapped cavitation region corresponds extremely well with the region over which the pressure amplitude generated by the HIFU transducer exceeds the cavitation threshold (continuous black line).

Figure 8:
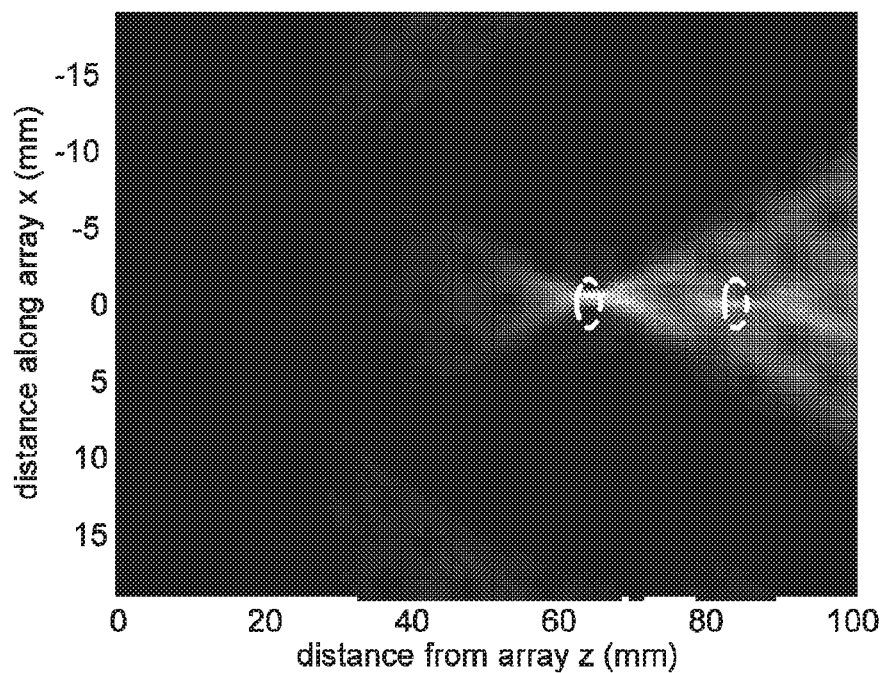
FIG. 8 is a two-dimensional mapping of two disjoint cavitation regions produced by the system of FIG. 2.

Finally, in the homogeneous two-channel phantom, cavitation was successfully instigated in the talc solution, creating two disjoint cavitation regions in the imaging plane. A passive map of this generated using (9) is shown in FIG. 8, in which the positions at which the channels intersect the image plane are indicated by the dashed circles and the cavitation can be seen as lighter areas in the region of the channels.

This embodiment therefore provides a system that can successfully locate a single cavitating source. More importantly, the setup allows mapping of spatially distributed cavitation while the HIFU signal is on. This provides a novel method of HIFU treatment monitoring that offers several advantages over currently used B-mode hyperechogenicity imaging.

It will be appreciated that the system of FIG. 1 can operate in the same passive modes as the system of FIG. 2, and can detect cavitation caused, for example, by a separate therapeutic transducer, or cavitation caused by other means.

In the context of non-invasive cancer therapy by HIFU, the occurrence of inertial cavitation can potentially be highly beneficial under moderate HIFU exposure conditions, since it can result in greatly enhanced rates of heat deposition. By contrast, the occurrence of stable cavitation, and in particular of larger, thermally induced bubbles, can be detrimental as it may result in asymmetric (or 'tadpole-shaped') lesion formation, overtreatment and undesirable prefocal damage. It is therefore beneficial to be able to characterize bubble activity during HIFU exposure, as well as to locate it as described above.

All types of bubble activity re-radiate part of the incident HIFU field at frequencies far removed from the main HIFU excitation frequency, making it possible to detect and qualify cavitation via spectral analysis of the noise emissions acquired passively during HIFU exposure. In particular, the onset of inertial cavitation is associated with a sudden increase in broadband noise, whilst larger cavities oscillating stably will result in increased emissions at harmonics, subharmonics and superharmonics of the main HIFU excitation frequency (collectively qualified as 'harmonics' hereafter). Furthermore, certain types of bubble activity induce a change in the local characteristic impedance of the target medium, resulting in a well-documented increase in the scattering and reflection of an actively generated incident diagnostic pulse that has become known as 'hyperecho' in B-mode images [Rabkin, B. A., et al., *Biological and physical mechanisms of HIFU-induced hyperecho in ultrasound images*. Ultrasound in Medicine & Biology, 2006. 32(11): p. 1721-1729].

The system of FIG. 2 is therefore arranged in one operating mode to combine passive and active cavitation detection schemes to provide real-time detection, classification, and localization of cavitation activity.

In this mode, the HIFU transducer 201 is driven at a 95% duty cycle using a function generator (Agilent 33220A) and a 55 dB fixed gain power amplifier (Electronics and Innovation A300). To test this mode, a polyacrylamide-based tissue-mimicking material containing dissolved bovine serum albumin was used as the target [Lafon, C, et al., *Gel phantom for use in high-intensity focused ultrasound dosimetry*. Ultrasound in Medicine and Biology, 2005. 31(10): p. 1383-1389]. In order to enable co-axial cavitation detection during HIFU exposure, a high-frequency, single-element diagnostic transducer (Panametrics V319) was placed inside the central opening of the HIFU transducer and positioned so that its focus overlaps with that of the therapy transducer. The diagnostic transducer is driven in pulse-echo mode using a pulser-receiver (JSR Ultrasonics DPR300) ensuring that the transmitted pulse is incident upon the HIFU focal region during the 5% off-time of the HIFU excitation. It will be appreciated that the 95% duty cycle enables the therapeutic HIFU transducer to be active for most of the time, with the 5% off time allowing for passive cavity detection and also 'pseudo active' cavity detection in which time of flight information can be determined for the passive detectors using the known time at which the therapeutic transducer 201 is turned on. The delay between that turn-on time and the first passive detection of cavitation at each of the detectors can be determined and used to determine the position of the cavitation events. It will be appreciated that one or more of the transducer elements 202 of the system of FIG. 2 can be used in a passive mode to operate in the same way.

A 400-microsecond time trace of the signal received by the axial cavitation detector was recorded every 50 ms throughout the HIFU exposure, the first 200 microseconds coinciding with the HIFU off-time, and the last 200 microseconds with the HIFU on-time. This makes it possible to utilize a single trace to reap the benefits of both an active and a passive detection scheme. The active scheme enables localization of bubble clouds by tracking the position of large reflections of the transmitted pulse. The passive scheme also provides information as to the position of the bubble cloud front nearest to the HIFU transducer, which can be identified by tracking the time-of-flight of the leading edge of the passively received signal, timed from the known time at which the HIFU transducer is turned on. More importantly, however, the passive scheme also enables classification of the type of cavitation activity being detected by using the spectral analysis technique described below.

In order to distinguish between the presence of inertial and stable cavitation, a Fast Fourier Transform (FFT) or similar spectral analysis algorithm is applied to each passively received signal, which enables separation of its harmonic and broadband noise components by digital filtering. This is achieved by applying bandpass filters of bandwidth 0.18 MHz around all multiples and sub-multiples of the HIFU excitation frequency: taking an inverse FFT of this signal provides the 'harmonic' time trace that only captures activity due to stable cavitation and, to a lesser extent, non-linear propagation through the phantom (the latter was not found to be significant in the tissue-mimicking material in the absence of bubbles). The signal remaining after applying 0.18 MHz notch filters to the original signal to remove the harmonics of the excitation frequency is purely representative of broadband noise. Similarly, its inverse FFT therefore provides a 'broadband' time trace that solely captures inertial cavitation activity.

Prior to experimentation, the inertial cavitation threshold in the tissue phantom was determined and found to be in the region of 1.5 MPa peak negative focal pressure. All pressures used in subsequent exposures were chosen to be well above this value.

Results

Passive Location Scheme

Figures 9A, 9B:
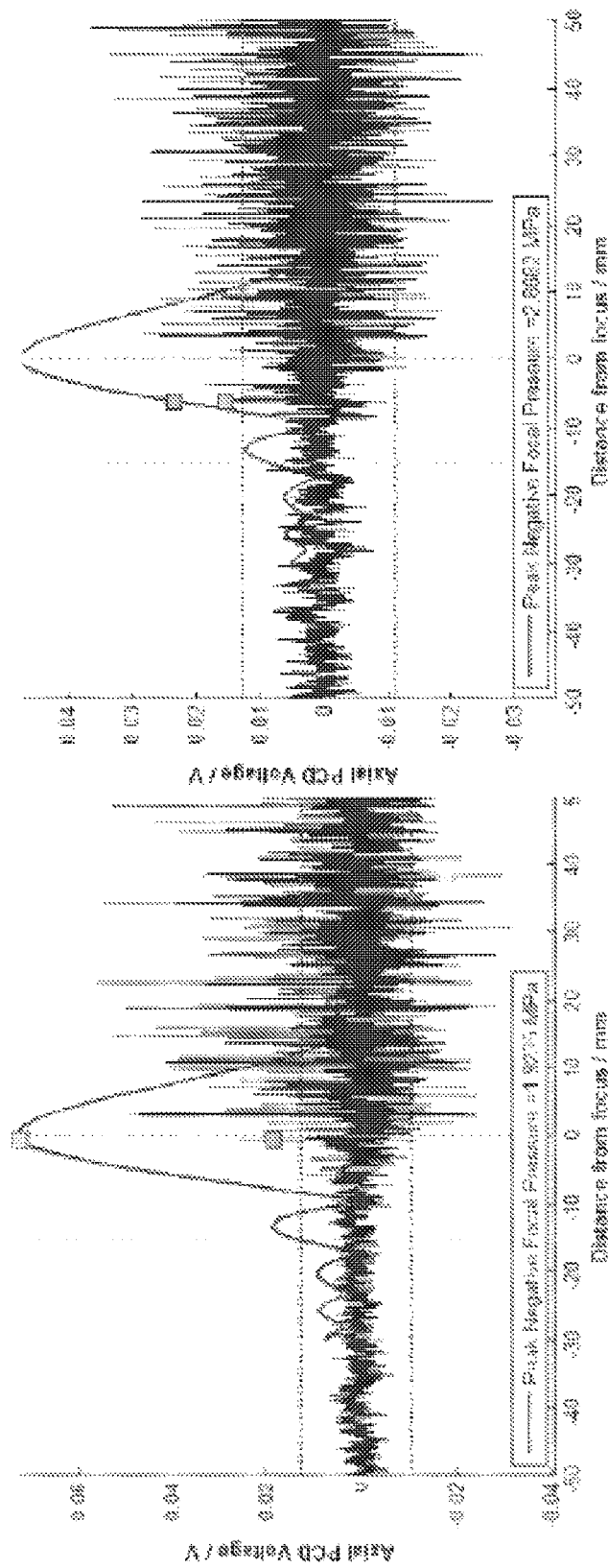
FIGS. 9a and 9b are graphs showing the broadband component of time traces obtained during HIFU exposure in the system of FIG. 2.

The principle of location of inertial cavitation activity using a passive detection scheme is illustrated in FIGS. 9a and 9b, which shows the time traces corresponding to the broadband component of the passively received signal during 1.1 MHz HIFU exposure of a tissue phantom at two different peak negative pressure amplitudes, chosen to be greater than the cavitation threshold.

The overlaid continuous line with a set of rounded peaks represents the axial pressure profile of the HIFU transducer measured using a hydrophone in water, whilst the leftmost dotted vertical line indicates the position of the phantom edge nearest to the HIFU transducer. The x-axis is converted into relative axial distance by using the speed of sound through the phantom and the square markers indicate the earliest occurrence of inertial cavitation activity. At the lower peak negative focal pressure amplitude (1.92 MPa), which is close the cavitation threshold, inertial cavitation activity is seen to onset at the position of maximum HIFU pressure. However, at the higher pressure amplitude (2.86 MPa), inertial cavitation is seen to onset some 10 mm ahead of the HIFU focus.

Passive Detection—Based Classification of Cavitation Activity

Figure 10:
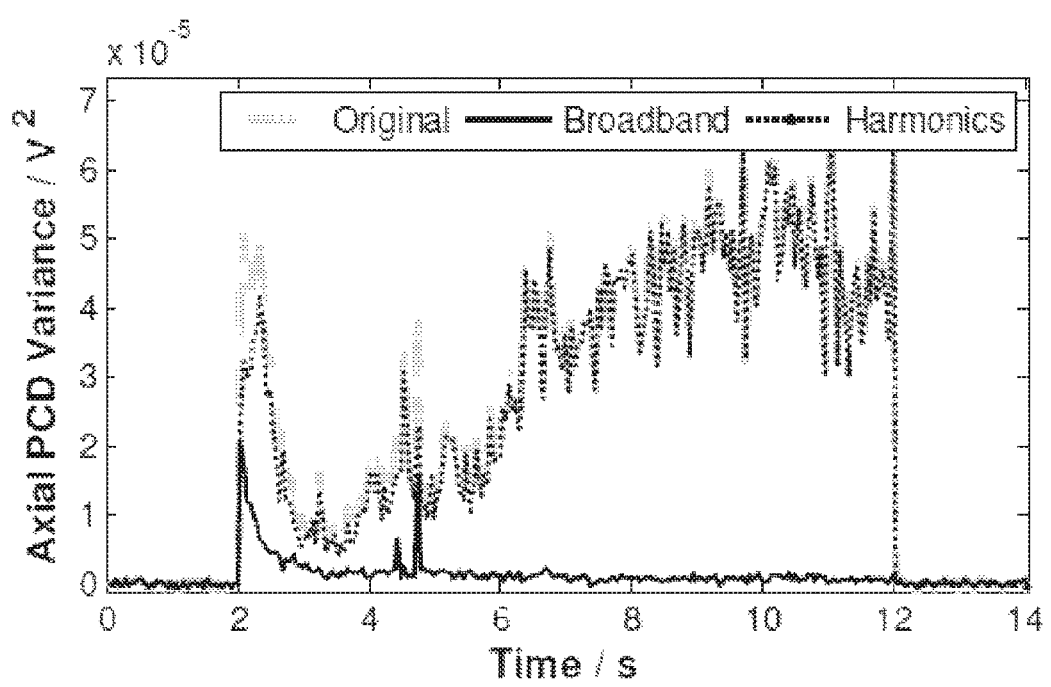
FIG. 10 is a graph showing broadband and harmonic components of the variance of a signal from one of the detectors in the system of FIG. 2 during HIFO exposure.

Continuous monitoring of the variance of passively received noise emissions during HIFU exposure provides a good indication of the evolution of bubble activity. Application of the digital filtering techniques described above prior to computing this variance makes it possible to qualify the different types of cavitation activity during HIFU exposure. This is illustrated in FIG. 10, which shows the broadband and harmonic components of the original, unfiltered passively received signal over time. At this high peak negative pressure amplitude (8.3 MPa), the broadband noise emissions associated with inertial cavitation activity occur immediately, but decay rapidly. This is most probably due to heat deposition in the phantom resulting in an increase in vapour pressure that inhibits bubble collapse. By contrast, stable cavitation activity is present throughout the exposure but increases dramatically beyond 4 seconds. This is likely due to the formation of boiling bubbles due to excessive heating of the phantom, which result in a sharp increase in the harmonic component of the passively received signal.

Combined Passive-Active Cavitation Detection

Lastly, the benefits of combining active and passive localization techniques are illustrated in FIGS. 11a to 11d. FIGS. 11a and 11b both show the variance of the passively received signal during a 30 second HIFU exposure (starting at t=2 s) at 3.5 MPa peak negative focal pressure. FIGS. 11c and 11d show the corresponding active trace at two different time instants over the course of the HIFU exposure, indicated by arrows on the passive trace in FIGS. 11a and 11b respectively. At t=2.80 s, passively detectable emissions are clearly present, but there is no signal detectable on the active trace. At t=5.05 s, the passively detectable emissions are considerably higher than at t=2.80 s, but there is now a large reflection visible on the active trace from the region coincident with the HIFU focus. The active scheme therefore seems more effective at detecting and localizing stable cavitation activity that tends to occur in the latter stages of HIFU exposure, whilst the passive scheme provides a more reliable indicator of inertial cavitation activity. Therefore, a combined active and passive system can characterize the detected cavitation as well as locating it.

Figure 12:
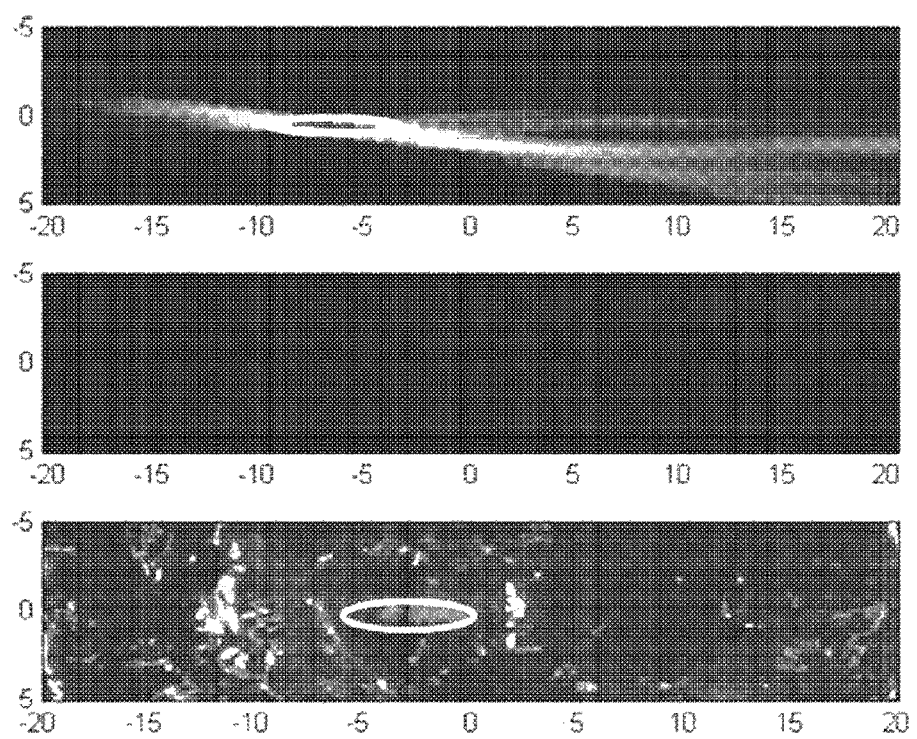
FIGS. 12 and 13 each show, for a respective exposure time, images of inertial cavitation, tissue boiling and tissue damage.

In order to demonstrate the effectiveness of passive imaging using an embodiment of the present invention, referring to FIG. 12, the top image is a cumulative passive broadband map indicative of inertial cavitation activity, the middle image is a cumulative passive harmonic map indicative of tissue boiling, and the bottom image is an image of histological damage in tissue, all following a 2-second ablative exposure of bovine liver tissue at a therapeutic ultrasound frequency of 1.1 MHz and at an intensity of 4 kW cm$^{-2}$ from the left. '0' on the x-axis indicates the predicted focus location of the therapeutic ultrasound beam. It can be seen that the passive mapping of broadband emissions successfully predicts the size and location of the resulting thermal lesion. The null harmonic map confirms the absence of boiling bubbles during this exposure.

Figure 13:
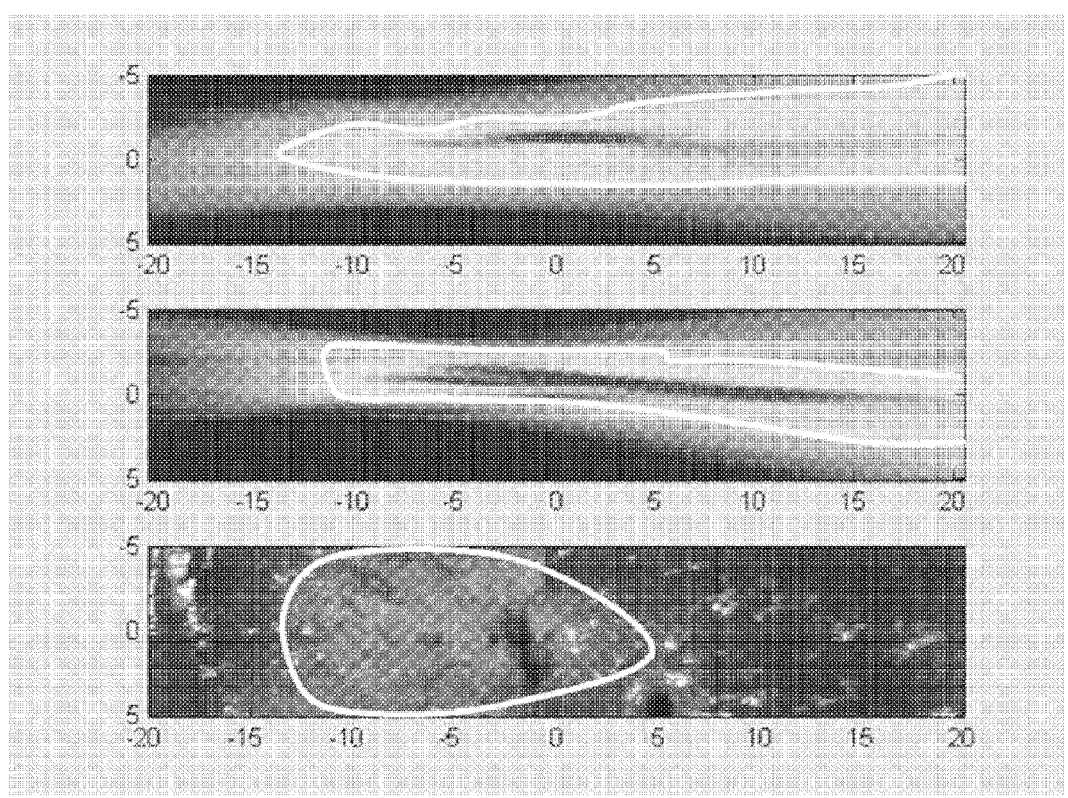

Referring to FIG. 13, similar images are shown for a 10-second exposure. It can be seen that the passive mapping technique successfully describes the movement of the thermal lesion towards the HIFU transducer. The 'pitting' visible inside the thermal lesion is also consistent with the presence of boiling bubbles, which have been successfully predicted by harmonic mapping. It will be appreciated that the system of FIG. 2 can operate in a number of different modes, either passive only to provide single bubble location or mapping of a region of cavitation, and in combined passive and active modes to characterize cavitation at the same time as locating or mapping it. Importantly, the system of FIG. 2 can locate or map, and therefore provide an image of or analyse, cavitation as it occurs during therapeutic ultrasound treatment.

In a further embodiment rather than a single array of detector elements that can be used as active or passive elements, in other embodiments there is an array of active elements and an array of passive elements. This provides the same range of operating modes.

In a further embodiment, a system similar to that of FIG. 2 can be used to control drug delivery or drug activity. It has been shown that acoustic vibration can greatly enhance the take-up and effect of various drugs, and the location, mapping, and characterization of bubbles in such applications is an important application of systems such as that of FIG. 2.

The invention claimed is:

1. Apparatus for locating a source of pressure waves, the source being located at a position in a subject, the source comprising at least one bubble, the apparatus comprising a pressure wave transducer configured to generate pressure waves at a generation frequency to generate cavitation including the at least one bubble, an array of pressure wave detectors configured to operate as passive detectors to generate output signals in response to the receipt of the pressure waves generated at the source over a broadband range of frequencies including harmonic components at harmonics of the generation frequency, and a processor configured to:
   receive the output signals from the detectors and
   determine from the signals the position of the source, following a removal of the harmonic components using filtering.

2. Apparatus according to claim 1 wherein the detectors are configured to detect pressure waves while the transducer is active and the processor is configured to determine the position of the source, which is the position of the source at a time when the transducer is active.

3. Apparatus according to claim 1 wherein the transducer is a therapeutic sound generator and the apparatus comprises a diagnostic pressure wave generator configured to generate pressure waves at a diagnostic frequency different from the generation frequency.

4. Apparatus according to claim 3 comprising an active pressure wave detector configured to detect pressure waves at the diagnostic frequency.

5. Apparatus according to claim 4 wherein the diagnostic pressure wave generator is a transducer which also acts as the active pressure wave detector.

6. Apparatus according to claim 4 wherein the processor is configured to receive signals from the active pressure wave detector.

7. Apparatus according to claim 5 wherein at least one of the passive pressure wave detectors is configured to operate alternatively as the active pressure wave detector.

8. Apparatus according to claim 7 wherein each of the passive pressure wave detectors is arranged to be operated alternatively as an active pressure wave detector.

9. Apparatus according to claim 1 wherein the source comprises a single bubble.

10. Apparatus according to claim 9 wherein, if the pressure waves arrive at the detectors at respective arrival times, the processor is configured to determine the position of the bubble from the arrival times of pressure waves at the detectors.

11. Apparatus according to claim 1 wherein the source comprises a plurality of bubbles and the processor is configured to process the signals to generate a map of the source.

12. Apparatus according to claim 11 wherein the processor is configured to generate the map by determining an intensity at each of a plurality of positions from the detector signals using a relationship of the form:

$$I = \frac{1}{T}\int_0^T \left[\left(\sum_i H_i(\tau)\right)^2 - \sum_i H_i(\tau)^2\right] d\tau$$

where $\tau$ represents a dummy integration variable used to integrate the plurality of signals $H_i(t)$, which represent the backpropagated signals received from the source(s) by each pressure wave detector, and T represents an arbitrary integration time interval.

13. Apparatus according to claim 1 wherein the processor is configured to turn on the pressure wave transducer and to measure the time at which the detectors detect pressure waves, thereby to determine the location of the source.

14. Apparatus according to claim 1 wherein the processor is configured to analyse at least two different frequency components of the signals to determine a characteristic of the source.

15. Apparatus according to claim 14 wherein one of the frequency components is a broadband component, and one of the frequency components includes at least one harmonic of a generator frequency.

16. Apparatus for locating a source of pressure waves, the source being located at a position in a subject, the source comprising at least one bubble, the apparatus comprising an array of pressure wave detectors configured to operate as passive detectors to generate output signals in response to the receipt of the pressure waves generated at the source, and a processor configured to receive the output signals from the detectors, to perform a cross correlation between the signals from a pair of the detectors by multiplication and integration of the signals from said pair of detectors, and to determine from the signals the position of the source using the cross correlation.

17. Apparatus according to claim 16 further comprising a pressure wave generator configured to generate pressure waves at a generator frequency, wherein the detectors are configured to detect pressure waves at least one detection frequency which is different from the generator frequency.

18. Apparatus according to claim 17 wherein the detectors are configured to detect pressure waves while the generator is active and the processor is configured to determine the position of the source, which is the position of the source at a time when the generator is active.

19. Apparatus according to claim 17 wherein the generator is a therapeutic sound generator and the apparatus comprises a diagnostic pressure wave generator configured to generate pressure waves at a diagnostic frequency different from the generator frequency.

20. Apparatus according to claim 16 wherein the source comprises a plurality of bubbles and the processor is configured to process the signals to generate a map of the source.

21. Apparatus for locating source of pressure waves, the source being located at a position in a subject, the source comprising at least one bubble, the apparatus comprising an array of pressure wave detectors configured to operate as passive detectors to generate output signals in response to the receipt of the pressure waves generated at the source, and a processor configured to:
receive the output signals from the detectors; and
determine from the signals the position of the source using a square of each of the signals.

22. Apparatus according to claim 21 further comprising a transducer arranged to generate pressure waves at a generation frequency, wherein the detectors are configured to detect pressure waves while the transducer is active and the processor is configured to determine the position of the source, which is the position of the source at a time when the transducer is active.

23. Apparatus according to claim 22 wherein the transducer is a therapeutic sound generator and the apparatus comprises a diagnostic pressure wave generator configured to generate pressure waves at a diagnostic frequency different from the generation frequency of the transducer.

24. Apparatus according to claim 21 wherein the source comprises a plurality of bubbles and the processor is configured to process the signals to generate a map of the source.

25. Apparatus according to claim 21 wherein the processor is configured to generate the map by determining an intensity at each of a plurality of positions from the detector signals using a relationship of the form:

$$I = \frac{1}{T}\int_0^T \left[\left(\sum_i H_i(\tau)\right)^2 - \sum_i H_i(\tau)^2\right] d\tau$$

where $\tau$ represents a dummy integration variable used to integrate the plurality of signals $H_i(t)$, which represent the backpropagated signals received from the source(s) by each pressure wave detector, and T represents an arbitrary integration time interval.

26. Apparatus for locating a pressure wave source comprising at least one bubble located at a position in a subject, the apparatus comprising a therapeutic pressure wave transducer configured to generate therapeutic pressure waves at a generation frequency to generate cavitation including the at least one bubble, a passive pressure wave detector arranged to detect a first arrival at the detector, at a first arrival time, of the pressure waves generated at the source and of a frequency which is different from the generation frequency and harmonics thereof, and output a signal in response to the pressure waves generated at the source, a display, and a controller configured to:
turn the pressure wave transducer on;
receive the signals from the detectors;
process the signal to identify a leading edge of the signal;
determine the delay between the time at which the therapeutic pressure transducer was turned on and the first arrival time;
determine, from said delay, the location of the source; and
control the display to indicate the location of the source.

27. The apparatus according to claim 26 further comprising at least one further detector, each said further detector being arranged to output a respective further signal in response to the pressure waves generated at the source, wherein the controller is configured to receive each said further signal, and to identify a further leading edge in each said further signal.

28. The apparatus according to claim 26 further comprising a filter arranged to remove components of the signal at the transmission frequency prior to processing the signal to identify said leading edge.

29. A method of locating a pressure wave source comprising at least one bubble located at a position in a subject, the method comprising:
   providing a pressure wave transducer arranged to generate therapeutic pressure waves at a generation frequency to generate cavitation including the at least one bubble,
   turning the pressure wave transducer on at a turn on time thereby to generate cavitation including the at least one bubble in the subject;
   detecting a first arrival at the detector, at a first arrival time, of the pressure waves generated at the source and of a frequency which is different from the generation frequency and harmonics thereof, and
   determining the delay between the turn on time and the first arrival time thereby to determine the location of the source.

30. The method according to claim 29 further comprising providing a passive pressure wave detector, receiving the pressure waves generated at the source and generating a signal in response to the pressure waves generated at the source using the detector, and wherein detecting said first arrival comprises identifying a leading edge in the signal.

31. The method according to claim 29 wherein the cavitation is inertial cavitation.

* * * * *